(12) United States Patent
Portmann et al.

(10) Patent No.: US 8,076,362 B2
(45) Date of Patent: *Dec. 13, 2011

(54) CRYSTAL MODIFICATION A OF 1-(2,6-DIFLUOROBENZYI)-1 H-1,2,3-TRIAZOLE-4-CARBOXAMIDE AND DOSAGE FORMS AND FORMULATIONS THEREOF

(75) Inventors: Robert Portmann, Pratteln (CH); Urs Christoph Hofmeier, St. Pantaleon (CH); Andreas Burkhard, Basel (CH); Walter Scherrer, Rheinfelden (CH); Martin Szelagiewicz, Münchenstein (CH)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 12/767,003

(22) Filed: Apr. 26, 2010

(65) Prior Publication Data

US 2010/0310655 A1    Dec. 9, 2010

Related U.S. Application Data

(63) Continuation of application No. 11/329,945, filed on Jan. 11, 2006, now Pat. No. 7,750,028, which is a continuation of application No. 10/787,528, filed on Feb. 26, 2004, now abandoned, which is a continuation of application No. 10/294,408, filed on Nov. 14, 2002, now abandoned, which is a continuation of application No. 09/125,329, filed as application No. PCT/EP98/03427 on Jun. 8, 1998, now Pat. No. 6,740,669.

(30) Foreign Application Priority Data

Jun. 10, 1997  (CH) .................................... 1404/97

(51) Int. Cl.
*A61K 31/4192* (2006.01)
*C07D 249/04* (2006.01)

(52) U.S. Cl. ........................................ 514/359; 548/255

(58) Field of Classification Search .................. 514/359; 548/255
See application file for complete search history.

(56) References Cited

U.S. PATENT DOCUMENTS

| | | | |
|---|---|---|---|
| 4,156,734 A | 5/1979 | Stone | |
| 4,536,518 A | 8/1985 | Welch | |
| 4,789,680 A | 12/1988 | Meier | |
| 5,248,699 A | 9/1993 | Sysko | |
| 6,156,907 A | 12/2000 | Portmann | |
| 6,455,556 B2 | 9/2002 | Portmann | |
| 6,740,669 B1 * | 5/2004 | Portmann et al. | 514/359 |

FOREIGN PATENT DOCUMENTS

| | | |
|---|---|---|
| EP | 0114347 | 12/1983 |
| EP | 0371564 | 11/1989 |
| EP | 812320 | 8/1996 |
| GB | 1511195 | 5/1978 |
| JP | A-02/214504 | 8/1990 |
| JP | A-05/155822 | 6/1993 |
| WO | 91/01724 | 2/1991 |
| WO | 95/12417 | 5/1995 |
| WO | 96/08485 | 3/1996 |
| WO | 96/09295 | 3/1996 |
| WO | 98/56773 | 12/1998 |

OTHER PUBLICATIONS

Material record "amorphous" internet (2010).*
Rouhi, A. Maureen. "The Right Stuff." Chem. & Engineering News, p. 32, (2003).
Concise Encyclopedia Chemistry, Walter de Gruyter, Berlin, New York, p. 82-83, (1993).
US Pharmacopia #23, National Formulary #18, p. 1843-1844, (1995).
Munzel, Prog Drug Res, 10: 227-230, (1966).
Munzel, Prog Drug Res, 14: 309-321, (1970).
Chemical Abstracts 105:48847, 1986.
Chemical Abstracts 106:182481, 1987.
Chemical Abstracts 108:118769, 1988.
Chemical Abstracts 90:192418, (1979).
Chemical Abstracts 77:168514, (1972).
Chemical Abstracts 80:100132, (1974).
Chemical Abstracts 80:6799, (1974).
Chemical Abstracts 94:180542, (1981).
Cheung, "Intra- and Inter-subject Variabilities of CGP 33101 After Replicate Single Oral Doses of Two 200-mg Tablets and 400-mg Suspension." Pharm. Res. 12(12): 1878-1882 (1995).
Chemical Abstracts 104:24095, (1986).
Ulicky, Comp Dic Phys Chem, 21, (1992).
Wyngaarden et al., Cecil Textbook Medicine. p. 48-55 (1983).
Full Development proposal CGP33101, (2009).
Meier, Characteristics of CGP33101 Kenndaten Fuer, (2009).

(Continued)

*Primary Examiner* — Celia Chang
(74) *Attorney, Agent, or Firm* — Montgomery, McCracken, Walker & Rhoads, LLP; Kristin M. Nevins

(57) ABSTRACT

The invention relates to dosage forms and formulations comprising the novel crystal modification A of the compound I-(2,6-difluorobenzyl)-I H-I,2,3-triazole-4-carboxamide, wherein crystal modification A is characterized by characteristic lines with interplanar spacings (d values) of 10.5 Å, 5.14 Å, 4.84 Å, 4.55 Å, 4.34 Å, 4.07 Å, 3.51 Å, 3.48 Å, 3.25 Å, 3.19 Å, 3.15 Å, 3.07 Å, and 2.81 Å, determined by means of an X-ray powder pattern. Dosage forms of crystal modification A of the compound I-(2,6-difluorobenzyl)-I H-I,2,3-triazole-4-carboxamide may be for oral or parenteral administration, in the form of a solid or liquid, and in a dosage range of 20 mg to less than 500 mg. Solid dosage forms comprise a tablet or capsule, and further comprise a pharmaceutically-acceptable carrier and film-coat.

21 Claims, 2 Drawing Sheets

OTHER PUBLICATIONS

Energy Temperature Diagram, (2009).
Dissolution profiles, (2009).
Merck Index, 13th Ed. Monograph No. 8373, (2001).
Presentation on patenting polymorphs by EPO examiner, (2006).
Kostic et al, Dopaminergic Ligands, Drugs Res, 44(1): 697-702, (1994).
EP431943 (Jun. 1991).
US3992378, (Nov. 1976).
DE4217952, (Dec. 1993).
WO9207847, (May 1992).
Chemical Abstracts, 95:50317r, (1981).
Cheung, "Intra- and Inter-Subject Variabilities of CGP33101 after Replicate Single Oral Doses of Two 200-mg Tablets and 400-mg Suspension," Pharmaceutical Research, 12(12):1878-79, (1995).
Rouan, "Automated analysis of a novel and-epileptic compound, CGP 33 101, and its metabolite, CGP 47 292, in body fluids by high-performance liquid chromatography and liquid-solid extraction," J. Chromatography B., 667:307-313, (1995).
Haleblian, "Pharmaceutical Applications of Polymorphism," J. Pharm. Sci., 58(8):911-929, (1969).
Leusen, "Ab initio prediction of polymorphs," J. Crystal Growth, 166:900-903, (1996).

* cited by examiner

CRYSTAL MODIFICATION A OF 1-(2,6-DIFLUOROBENZYI)-1 H-1,2,3-TRIAZOLE-4-CARBOXAMIDE AND DOSAGE FORMS AND FORMULATIONS THEREOF

RELATED U.S. APPLICATION DATA

This application is a continuation of U.S. application Ser. No. 11/329,945 filed on Jan. 11, 2006, now U.S. Pat. No. 7,750,028 which is a continuation of application Ser. No. 10/787,528 filed on Feb. 26, 2004, now abandoned which is a continuation of application Ser. No. 10/294,408, filed on Nov. 14, 2002, now abandoned, which is a continuation of application Ser. No. 09/125,329, filed on Sep. 8, 1998, now U.S. Pat. No. 6,740,669, filed as 371 of international Application No. PCT/EP98/03427, filed on Jun. 8, 1998. The contents of which are herein incorporated by reference, respectively, in their entireties.

BACKGROUND OF THE INVENTION

The compound I-(2,6-difluorobenzyl)-I H-I,2,3-triazole-4-carboxamide of the formula

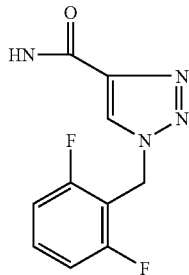

is described in the European Patent Application with the Publication No. 0 199 262 A2 (EP 199262), for example in Example 4. Valuable pharmacological properties are attributed to this compound; thus, it can be used, for example, as an antiepileptic. The compound I-(2,6-difluorobenzyl)-I H-I,2,3-triazole-4-carboxamide is obtained according to EP 199262, starting from 2,6-difluorobenzyl azide via the formation of I-(2,6-difluorobenzyl)-I H-I,2,3-triazole-4-carboxylic acid, the procedure being analogous to Example 2.

EP 199262 provides no information at all about possible crystal modifications obtained. If the method according to the Example 4 is used in conjunction with Example 2, the crude I-(2,6-difluorobenzyl)-I H-I,2,3-triazole-4-carboxamide product obtained is finally crystallized from ethanol. However, EP 199262 gives no indication that such recrystallization is specifically to be applied, or on particular conditions that might be adopted. It has now surprisingly been found that the different crystal modifications (polymorphism) characterized below can be prepared by choice of specially selected process conditions, for example through the choice of an appropriate solvent for the recrystallization or the duration of the recrystallization.

DESCRIPTION OF THE INVENTION 1-(2,6-difluorobenzyl)-1H-1,2,3-triazole-4-carboxamide can be obtained in the novel crystal modifications A, A', B and C. These crystal modifications differ with respect to their thermodynamic stability, in their physical parameters, such as the absorption pattern of IR and Raman spectra, in X-ray structure investigations and in their preparation processes.

The invention relates to the novel crystal modifications A and A', their preparation and use in pharmaceutical preparations comprising this crystal modification.

The modification A', compared with A, has defects in the crystal lattice. These are detectable, for example, by X-ray analysis, e.g. by smaller line spacings with otherwise predominantly identical lines or bands.

The novel crystal modification A of I-(2,6-difluorobenzyl)-I H-I,2,3-triazole-4-carboxamide melts at 242° C. (239-245° C.).

Figure 1:
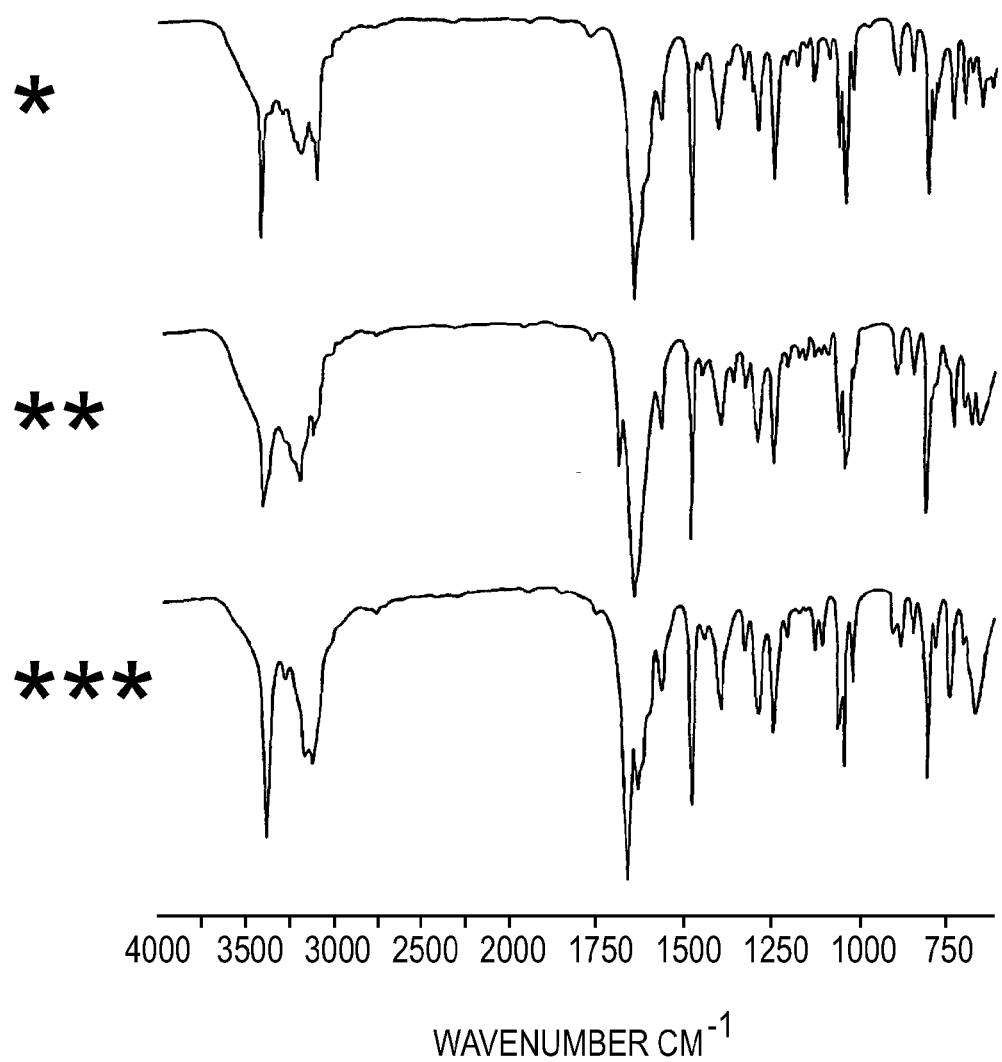
FIG. 1 shows the FT-IR spectra of the KBr pellets of modifications A, B and C.

In the FT infrared (FT-IR) spectrum (KBr pellet-transmission method), modification A or A' differs from modifications B and C predominantly in the shape and in the relative intensity of many bands. Particularly characteristic are the bands at 3412 $cm^{-1}$ and 3092 $cm^{-1}$ [cf. FIG. 1], which are not present in the FT-IR spectra of the modifications B and C. In the range 4000-600 $cm^{-1}$, inter alia the following bands are obtained for modification. A: 3412, 3189, 3092, 1634, 1560, 1473, 1397, 1325, 1300, 1284, 1235, 1125, 1053, 1036, 1014, 885, 840, 799, 781, 723, 688 and 640 $cm^{-1}$. For example, the apparatus IFS 88 (Bruker) can be used for the recording of each of the FT-IR spectra.

Figure 2:
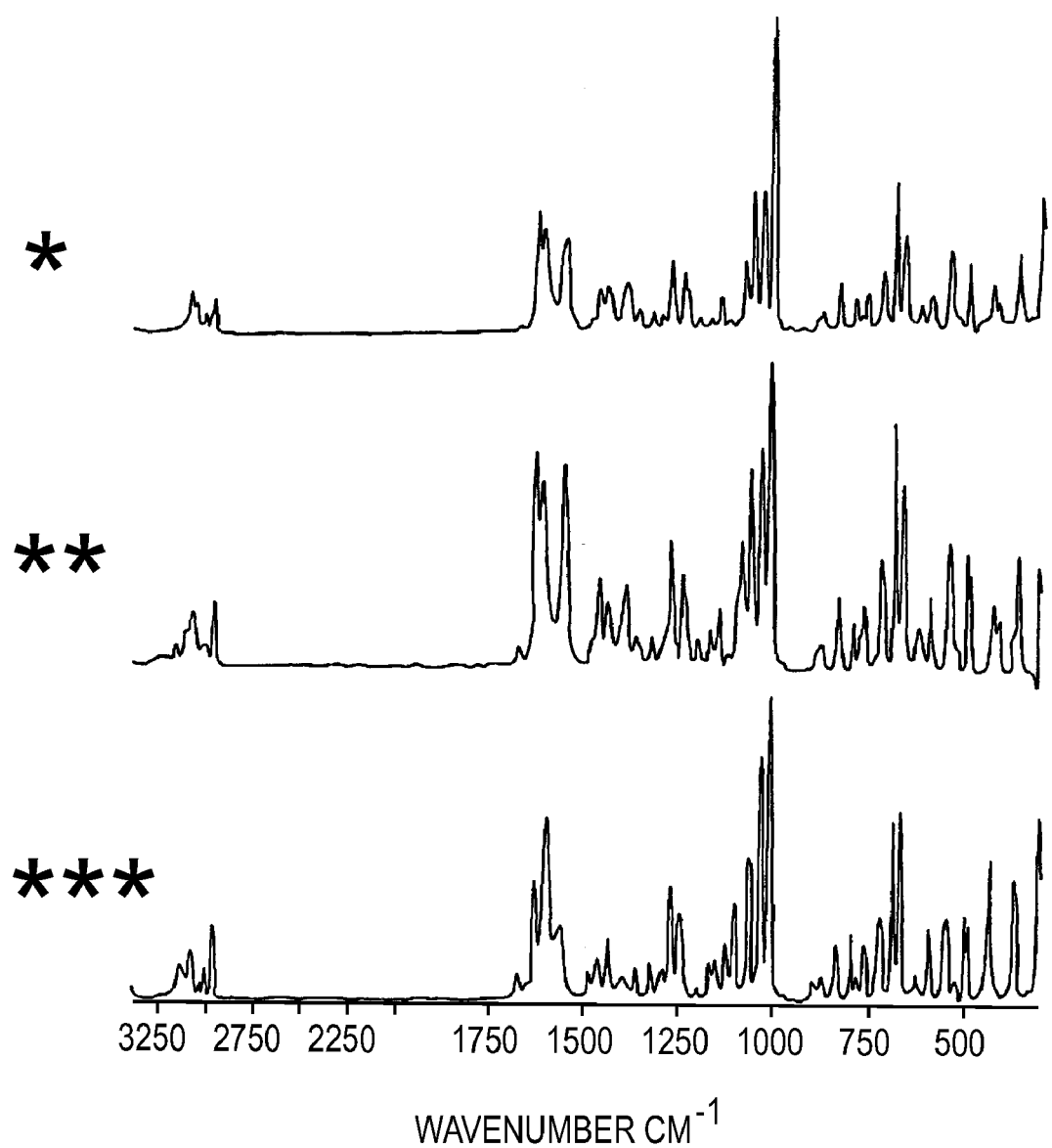
FIG. 2 shows the FT-Raman spectra of the powder of modification A, B and C. In both Figures, the modification A is denoted by the symbol *, the modification B by the symbol  and the modification C by the symbol *.

In the FT Raman spectrum (powder-reflection method 180°), the modification A or A differs from modifications B and C predominantly in the shape and in the relative intensity of many bands. Particularly characteristic are the band at 1080 $cm^{-1}$ [cf. FIG. 2], which is not present in the Raman spectra of the modifications B and C. In the range 3400-300 $cm^{-1}$, inter alia the following bands are obtained for the modification A: 3093, 2972, 1628, 1614, 1558, 1465, 1446, 1393, 1279, 1245, 1147, 1080, 1061, 1036, 1014, 840, 724, 691, 667, 550, 499, 437 and 368 $cm^{-1}$. For example, the apparatus RFS 100 (Bruker) can be used for the recording of each of the FT Raman spectra.

The novel modification A has an X-ray powder pattern with characteristic lines with interplanar spacings (d values) of 10.5 Å, 5.14 Å, 4.84 Å, 4.55 Å, 4.34 Å, 4.07 Å, 3.51 Å, 3.48 Å, 3.25 Å, 3.19 Å, 3.15 Å, 3.07 Å, 2.81 Å [cf. Table 1]. The measurement can be carried out, for example, in transmission geometry on an FR 552 Guinier camera from Enraf-Nonius, Delft (The Netherlands), using copper $K\alpha_1$ radiation (wavelength $\lambda$=I.54060 Å). The patterns recorded on X-ray film were measured using an LS-18 line scanner from Johannsson, Taby (Sweden) and evaluated using the Scanpi software (P. E. Werner, University of Stockholm).

Characteristic for the novel modification A is the thermogram in differential scanning calorimetry. It has an endothermic peak in the range from 230° C. to 260° C. The peak temperature is 239-245° C., and the endothermic signal is 209 J/g+/−10 J/g. The measurement was carried out on a Perkin Elmer DSC 7 in a closed pan with a heating rate of 20 K/minute. The typical sample quantity is about 4 mg. As a typical distinguishing feature compared with the modifications B and C, the thermogram of the modification A has no further thermal signal.

Crystals of the modification A' have the same crystal structure as modification A. They differ from the modification A in the X-ray powder pattern in that they have slightly smaller line spacings between specific pairs of lines. These are the pairs of lines with the following interplanar spacings: 3.68 Å and 3.64 Å, 3.51 Å and 3.48 Å, 3.19 Å and 3.15 Å.

In the FT-IR spectrum (KBr pellet—transmission method), the modification B differs from the modification A or A' and C predominantly in the shape and in the relative intensity of many bands. Particularly characteristic is a band at 1678 cm$^{-1}$ [cf. FIG. 1], which is not to be observed in the corresponding spectra of the modifications A and C. In the range 4000-600 cm$^{-1}$, inter alia the following bands are obtained for the modification B: 3404, 3199, 3125, 1678, 1635, 1560, 1475, 1393, 1357, 1322, 1286, 1237, 1051, 1036, 1028, 889, 837, 800, 719, 667 and 645 cm$^{-1}$. For example, the apparatus IFS 85 (Bruker) can be used for recording of each of the FT-IR spectra.

In the FT Raman spectrum (powder-reflection method 180°), the modification B differs from the modifications A or A' and C predominantly in the shape and in the relative intensity of many bands. Particularly characteristic are the bands at 3166 cm$^{-1}$ and 1086 cm$^{-1}$ [cf. FIG. 2], which are not present in the Raman spectra of the modifications A and C. In the range 3400-300 cm$^{-1}$, inter alia the following bands are obtained for the modification B: 3166, 3089, 2970, 1678, 1628, 1614, 1559, 1464, 1441, 1391, 1275, 1244, 1147, 1086, 1062, 1036, 1014, 839, 773, 724, 690, 668, 595, 549, 500, 493, 430 and 365 cm$^{-1}$. For example, the apparatus RFS 100 (Bruker) can be used for recording of each of the FT Raman spectra.

The modification B has an X-ray powder pattern with characteristic lines with interplanar spacings (d values) of 11.0 Å, 8.3 Å, 5.18 Å, 4.88 Å, 4.80 Å, 4.42 Å, 4.33 Å, 4.19 Å, 4.12 Å, 3.81 Å, 3.50 Å, 3.41 Å, 3.36 Å, 3.32 Å, 3.28 Å, 3.24 Å, 3.05 Å, 2.83 Å [cf. Table 1].

In the thermogram in differential scanning calorimetry, the modification B has, in addition to an endothermic signal in the range from 230° C. to 260° C. (peak temperature 239-245° C.), a weak thermal signal at 205° C. (180°-220° C.) as a typical distinguishing feature compared with the modifications A or A' and C.

In the FT-IR spectrum (KBr pellet—transmission method), the modification C differs from the modifications A or A' and B predominantly in the shape and in the relative intensity of many bands. Particularly characteristic is a band at 3137 cm$^{-1}$ [cf. FIG. 1], which is not to be observed in the corresponding spectra of the modifications A and B.

In the range 4000-600 cm$^{-1}$, inter alia the following bands are obtained for the modification C: 3396, 3287, 3137, 1657, 1631, 1602, 1559, 1475, 1392, 1323, 1287, 1237, 1122, 1104, 1047, 1035, 1012, 876, 839, 797, 773, 729 and 653 cm$^{-1}$. For example, the apparatus IFS 85 (Bruker) can be used for recording of each of the FT-IR spectra.

In the FT Raman spectrum (powder-reflection method 180°), the modification C differs from the modifications A or A' and B predominantly in the shape and in the relative intensity of many bands. Particularly characteristic are the bands at 3137 cm$^{-1}$ and 1602 cm$^{-1}$ [cf. FIG. 2], which are not present in the Raman spectra of the modifications A and B. In the range 3400-300 cm$^{-1}$, inter alia the following bands are obtained for the modification C: 3137, 3080, 3012, 2971, 1673, 1629, 1602, 1561, 1436, 1271, 1248, 1105, 1065, 1035, 1013, 839, 800, 767, 726, 690, 672, 593, 549, 500, 492, 435 and 370 cm$^{-1}$. For example, the apparatus RFS 100 (Bruker) can be used for recording of each of the FT Raman spectra.

The modification C has an X-ray powder pattern with characteristic lines with interplanar spacings (d values) of 9.0 Å, 4.73 Å, 4.65 Å, 3.75 Å, 3.54 Å, 3.42 Å, 3.25 Å [cf. Table 1]. In the thermogram in differential scanning calorimetry, the modification C has, in addition to an endothermic signal in the range of 230° C. to 260° C. (peak temperature 239-245° C.), a very broad, weak, exothermic signal in the region of 180° C. compared with the modifications A or A' and B.

TABLE 1

Characterization of the modifications A, B and C (X-ray powder patterns):

| Modification A: | | Modification B: | | Modification C: | |
| --- | --- | --- | --- | --- | --- |
| d [Å] | Intensity | d [Å] | Intensity | d [Å] | Intensity |
| 10.9 | weak | 11.0 | medium | 9.0 | medium |
| 10.5 | medium | 8.3 | medium | 7.0 | weak |
| 6.6 | weak | 8.1 | very weak | 5.49 | weak |
| 5.63 | weak | 5.68 | very weak | 5.11 | very weak |
| 5.25 | weak | 5.18 | very strong | 4.80 | weak |
| 5.14 | medium | 5.11 | weak | 4.73 | strong |
| 4.94 | weak | 4.88 | medium | 4.65 | very strong |
| 4.84 | very strong | 4.80 | strong | 4.47 | very weak |
| 4.55 | strong | 4.71 | very weak | 4.19 | very weak |
| 4.42 | very weak | 4.61 | weak | 4.11 | very weak |
| 4.34 | medium | 4.45 | weak | 3.98 | very weak |
| 4.23 | very weak | 4.42 | strong | 3.83 | very weak |
| 4.16 | weak | 4.33 | very strong | 3.75 | strong |
| 4.07 | medium | 4.19 | medium | 3.73 | weak |
| 4.01 | weak | 4.12 | strong | 3.54 | medium |
| 3.68 | very weak | 4.09 | weak | 3.50 | weak |
| 3.64 | very weak | 3.99 | very weak | 3.42 | strong |
| 3.60 | weak | 3.95 | very weak | 3.25 | medium |
| 3.56 | weak | 3.84 | weak | 2.88 | very weak |
| 3.51 | medium | 3.81 | medium | 2.80 | very weak |
| 3.48 | medium | 3.65 | weak | 2.74 | very weak |
| 3.38 | very weak | 3.61 | very weak | 2.67 | very weak |
| 3.25 | strong | 3.58 | very weak | 2.64 | weak |
| 3.19 | medium | 3.54 | weak | | |
| 3.15 | medium | 3.50 | medium | | |
| 3.11 | weak | 3.47 | very weak | | |
| 3.07 | medium | 3.41 | medium | | |
| 2.93 | very weak | 3.36 | very strong | | |
| 2.87 | very weak | 3.32 | strong | | |
| 2.81 | medium | 3.28 | medium | | |
| 2.76 | weak | 3.24 | medium | | |
| 2.73 | very weak | 3.10 | weak | | |
| 2.68 | weak | 3.07 | weak | | |
| 2.62 | very weak | 3.05 | medium | | |
| 2.53 | weak | 2.93 | weak | | |
| 2.43 | weak | 2.88 | weak | | |
| 2.40 | very weak | 2.87 | very weak | | |
| | | 2.83 | medium | | |
| | | 2.66 | weak | | |
| | | 2.63 | very weak | | |
| | | 2.55 | weak | | |
| | | 2.50 | weak | | |
| | | 2.46 | weak | | |
| | | 2.44 | weak | | |
| | | 2.37 | weak | | |
| | | 2.35 | weak | | |

Single Crystal X-Ray Analysis:

Crystal quality and unit cell of modifications A, B, and C were verified by Weissenberg and precession photographs. The intensities were measured on a four-axis Nonius CAD-4 diffractometer. The structures were solved with the SHELXS-97 and refined with the SHELXL-97 software.

Modification A

Space group: Pna$2_1$—orthorhombic

Cell Dimensions:

$a$=24.756(5) Å $b$=23.069(4) Å $c$=5.386(1) Å

$V$=3075.9 Å$^3$ $Z$=12 $D_x$=1.543 gcm$^3$ $V$ per formula: $V_z$=256.3 Å$^3$ 9011 unique reflections; 2479 thereof significant with I>2 σ(I). 557 parameters refined. Position of all H atoms found by difference Fourier maps and refined isotropically. Reliability index $R_1$: 3.65% ($wR_2$ for all 9011 reflections: 11.34%).

Modification B
Space group: P⁻1—triclinic
Cell Dimensions:

$$a=5.326(I) \text{ Å } b=11.976(2) \text{ Å } c=17.355(3) \text{ Å}$$

$$\alpha=107.22(3)° \quad \beta=92.17(3)° \quad \gamma=102.11(3)°$$

$$V=1027.9 \text{ Å}^3 \quad Z=4 \quad D_x=1.539 \text{ gcm}^3$$

$$V \text{ per formula } V_z=257.0 \text{ Å}^3$$

4934 unique reflections; 834 thereof significant with I>2σ(I). 232 parameters refined. Position of all H atoms found by difference Fourier maps and refined isotropically. Reliability index $R_1$: 4.20% ($wR_2$ for all 4934 reflections: 7.93%).

Modification C
Space group: P2₁/C—monoclinic
Cell Dimensions:

$$a=10.982(2) \text{ Å } b=5.350(I) \text{ Å } c=17.945(3) \text{ Å}$$

$$\beta=91.59(1)°$$

$$V=1053.9 \text{ Å}^3 \quad Z=4 \quad D_x=1.501 \text{ gcm}^{-3}$$

$$V \text{ per formula: } V_z=263.5 \text{ Å}^3$$

3073 unique reflections; 1071 thereof significant with I>2σ(I). 187 parameters refined. Position of all H atoms found by difference Fourier maps and refined isotropically. Reliability index $R_1$: 5.02% ($wR_2$ for all 3073 reflections: 14.55%).

Modifications A, A', B and C have valuable pharmacological properties; in particular, they can be used for the treatment of epilepsy.

The modification A or A' has significant advantages compared with the modification B and compared with the modification C. Thus, for example, comprehensive thermodynamic investigations, such as thermomicroscopy, X-ray powder diffractometry, DSC, solubility tests and other experiments, have shown that the modification A or A' surprisingly has substantially better thermodynamic stability than the modifications B and C. Modification C, which can be obtained only under specific conditions, is the least stable of the three modifications. The crystals of the modification C are converted into modification B at as low as room temperature within a few weeks. The modification C is converted either into the modification A or A' or into the modification B, depending on experimental conditions.

It is particularly important for drug that its pharmaceutical formulation ensures high and reproducible stability over a long period. These preconditions are fulfilled by incorporation of the compound I-(2,6-difluorobenzyl)-I H-I,2,3-triazole-4-carboxamide of the crystal modification A or A', owing to its high thermodynamic stability. In particular, this is displayed in a solid pharmaceutical dosage form.

A constant stability also permits reproducible bio-availability of an active ingredient. If an active ingredient is subjected to a conversion process, this may readily also cause the bioavailability to fluctuate, which is undesirable. Accordingly, pharmaceutical active ingredients or polymorphic forms thereof which are of primary interest for pharmaceutical developments are those which exhibit high stability and do not have the above-mentioned disadvantages. The crystal modification A or A' fulfils these preconditions.

Furthermore, the modification A or A' has, for example, a slower dissolution rate in water or in gastric fluid (so-called "slow-release effect"). This effect can be utilized primarily for long-term therapy where a slow or delayed release is desired.

The invention relates to the modification A of I-(2,6-difluorobenzyl)-I H-I,2,3-triazole-4-carboxamide, characterized by the following absorptions in the infrared spectrum (KBr pellet—transmission method): bands at 3092 cm⁻¹ and 3412 cm⁻¹.

The invention relates to the modification A of I-(2,6-difluorobenzyl)-I H-I,2,3-triazole-4-carboxamide, characterized by characteristic lines with interplanar spacings (d values) of 10.5 Å, 5.14 Å, 4.84 Å, 4.55 Å, 4.34 Å, 4.07 Å, 3.51 Å, 3.48 Å, 3.25 Å, 3.19 Å, 3.15 Å, 3.07 Å and 2.81 Å, determined by means of an X-ray powder pattern.

The invention relates to the modification A of I-(2,6-difluorobenzyl)-I H-I,2,3-triazole-4-carboxamide, characterized by the characteristic lines with interplanar spacings (d values) as shown in Table 1.

The invention relates to the modification A of I-(2,6-difluorobenzyl)-I H-I,2,3-triazole-4-carboxamide, characterized by an endothermic peak in the range from 230° C. to 260° C., the peak temperature being 239-245° C. and the endothermic signal being 209 J/g+/−10 J/g.

Furthermore, the invention relates to the crystal modification A' which, compared with modification A, has defects in the crystal lattice.

The invention relates to the modification A' which, compared with modification A, has smaller line spacings between the pairs of lines with interplanar spacings 3.68 Å and 3.64 Å, 3.51 Å and 3.48 Å, and 3.19 Å and 3.15 Å.

The invention relates to the essentially pure form of the modification A or A' of I-(2,6-difluorobenzyl)-I H-I,2,3-triazole-4-carboxamide. The term "essentially pure form" means purity of >95%, in particular >98%, primarily >99%, based on the modification A or A'.

The invention relates to pharmaceutical preparations comprising the modification A or A' of I-(2,6-difluorobenzyl)-I H-I,2,3-triazole-4-carboxamide. The invention relates in particular to corresponding pharmaceutical preparations for the treatment of epilepsy and sub-indications thereof. The invention relates to the use of the modification A or A' of I-(2,6-difluorobenzyl)-I H-I,2,3-triazole-4-carboxamide for the preparation of pharmaceutical preparations, in particular for the treatment of epilepsy and sub-indications thereof.

The novel modification A or A' of I-(2,6-difluorobenzyl)-I H-I,2,3-triazole-4-carboxamide can be used, for example, in the form of pharmaceutical preparations which comprise a therapeutically effective amount of the active ingredient, if desired together with inorganic or organic, solid or liquid, pharmaceutically usable carriers, which are suitable for enteral, for example oral, or parenteral administration. Furthermore, the novel modification A or A' of I-(2,6-difluorobenzyl)-I H-I,2,3-triazole-4-carboxamide can be used in the form of preparations which can be administered parenterally or of infusion solutions. The pharmaceutical preparations may be sterilized and/or may comprise excipients, for example preservatives, stabilizers, wetting agents and/or emulsifiers, solubilizers, salts for regulating the osmotic pressure and/or buffers. The present pharmaceutical preparations comprise from about 0.1% to 100%, in particular from about 1% to about 50%, of lyophilisates to about 100% of the active ingredient.

The invention also relates to the use of modification A or A' of I-(2,6-difluorobenzyl)-I H-I,2,3-triazole-4-carboxamide as a drug, preferably in the form of pharmaceutical preparations. The dosage may depend on various factors, such as method of administration, species, age and/or individual condition. The doses to be administered daily are between about 0.25 and about 10 mg/kg in the case of oral administration, and preferably between about 20 mg and about 500 mg for warm-blooded species having a body weight of about 70 kg.

The preparation of modification A or A' is carried out, for example, as described in the embodiments below.

Preparation of I-(2,6-difluorobenzyl)-I H-I,2,3- of triazole-4-carboxamide

Example 1

A suspension of methyl I-(2,6-difluorobenzyl)-I H-I,2,3-triazole-4-carboxylate (about 62 parts by weight), methanol (475.2 parts by weight) and anhydrous ammonia (29.4 parts by weight) is stirred for about 24 hours at 50-55° C. in a closed vessel. The suspension is cooled to about 20° C. and stirred for about a further 2 hours. The product is isolated by filtration, washed with methanol (240 parts by weight) and dried at 40-60° C. in vacuo. Yield: 57.2 parts by weight=98%. Modification A.

The starting compounds can be prepared, for example, as follows:

A mixture of I-(2,6-difluorobenzyl)-I H-I,2,3-triazole-4-carboxylic acid (167.1 parts by weight), methanol (552 parts by weight) and 96% sulfuric acid (35.7 parts by weight) is stirred for about 5 hours at 60-66° C. The suspension is cooled to about 20° C. and stirred for about a further 2 hours. The product is isolated by filtration and washed with methanol (198 parts by weight). A yield of about 160 parts by weight is obtained by drying at 40-60° C. in vacuo.

Example 2

1 N sodium hydroxide solution (0.11 ml) is added to a mixture of 4-Cyano-I-(2,6-difluorobenzyl)-I H-I,2,3-triazole (2.20 g) and water (44 ml) at an external temperature of 95-10° C. while stirring. After 90 minutes, the suspension is cooled to 10° C. and the product is isolated by filtration, washed with water and dried at about 60° C. in vacuo. I-(2,6-difluorobenzyl)-I H-I,2,3-triazole-4-carboxamide is obtained in this manner; yield: 99.2% by weight. Modification A.

The starting material can be prepared, for example, as follows:

4-Cyano-I-(2,6-difluorobenzyl)-I H-I,2,3-triazole

A mixture of 2,6-difluorobenzyl azide (34.2 g), 2-chloroacrylonitrile (17.73 g) and water. (125 ml) is stirred for 24 hours at about 80° C. By increasing the external temperature to about 130° C., excess 2-chloroacrylonitrile is distilled off. The semisolid mixture is cooled to about 40° C., cyclohexane (50 ml) is added to the suspension and the mixture is brought to about 20° C. and stirred for about 2 hours. The product is isolated by filtration and washed with cyclohexane (75 ml) and then with water (50 ml). The moist product is mixed with water (100 ml), the suspension is filtered and the product is washed with water (50 ml) and dried at about 60° C. in vacuo. Yield: 38.04 g=86%.

Examples of the Recrystallization of I-(2,6-difluorobenzyl)-I H-I,2,3-triazole-4-carboxamide Example 3

I-(2,6-difluorobenzyl)-I H-I,2,3-triazole-4-carboxamide (75.0 g) is dissolved in formic acid (360 ml) at 50-55° C. by stirring. The solution is discharged in the course of 1 hour onto stirred methanol (375 ml) at about 20° C., a suspension forming. After stirring has been continued for 2 hours at about 20° C., the product is isolated by filtration, washed with methanol (750 ml) and dried at about 60° C. in vacuo. Yield: 69.6 g=92.8%. Modification A.

Example 4

I-(2,6-difluorobenzyl)-I H-I,2,3-triazole-4-carboxamide (22.86 kg) is dissolved in formic acid (111.6 kg) at 58-63° C. while stirring. The solution is discharged in the course of about 2 hours onto stirred methanol (131.9 1) at 20-25° C., after which washing with formic acid (7.6 kg) is carried out. A suspension forms. After stirring has been continued for at least 3 hours at about 20° C., the product is isolated by filtration and washed with methanol (187.5 1). By drying in vacuo at about 60° C., the product is obtained as modification A in a yield of 93-94%.

Example 5

I-(2,6-difluorobenzyl)-I H-I,2,3-triazole-4-carboxamide (pure active ingredient; 4.0 g) is dissolved in 96% ethanol (500 ml, without denaturing agent) at about 80° C. while stirring. The solution is filtered into a suction bottle (1 liter) at about 20° C. (glass suction filter, pore size 10-20/μm), a suspension forming. After stirring has been continued for 5 minutes at about 20° C. and for 15 minutes at about 0° C., the product is isolated by filtration (about 0° to about 20° C.). The solvent-moist product (9.6 g) is investigated without subsequent drying. Modification A'.

Formulation Example 1

Film-coated tablets each containing, for example, 100, 200 or 400 mg of modification A or A' of I-(2,6-difluorobenzyl)-I H-I,2,3-triazole-4-carboxamide with the following composition per dosage unit:

|  | mg | mg | mg |
|---|---|---|---|
| Core material | | | |
| Active ingredient | 100.00 | 200.00 | 400.00 |
| Anhydrous, colloidal silica | 0.88 | 1.75 | 3.5 |
| Microcrystalline cellulose | 36.62 | 73.25 | 146.50 |
| Hydroxypropylmethyl-cellulose | 5.00 | 10.00 | 20.00 |
| Lactose | 20.00 | 40.00 | 80.00 |
| Magnesium stearate | 2.00 | 4.00 | 8.00 |
| Maize starch | 10.00 | 20.00 | 40.00 |
| Sodium carboxymethylcellulose | 5.00 | 10.00 | 20.00 |
| Sodium lauryl sulfate | 0.50 | 1.00 | 2.00 |
| Film coat | | | |
| Hydroxypropylmethyl cellulose | 3.22 | 6.43 | 12.87 |
| Red iron oxide | 0.04 | 0.09 | 0.18 |
| Polyethylene glycol 8000, flakes | 0.58 | 1.16 | 2.32 |
| Talc | 2.33 | 4.66 | 9.31 |
| Titanium dioxide | 0.83 | 1.66 | 3.32 |

The active ingredient is granulated with de-mineralized water. Milled lactose, maize starch, Avicel PH 102, cellulose-HP-M-603 and sodium lauryl sulfate are added to the above mixture and granulated with de-mineralized water.

The moist material is dried and milled. After the addition of the remaining ingredients, the homogeneous mixture is compressed to give tablet cores having the stated active ingredient content.

The tablet cores are coated with the film coat which is formed from the appropriate ingredients, the latter being dissolved or being suspended in water or in small amounts of ethanol with 5% of isopropanol.

We claim:

1. A solid dosage form for administration comprising an amount ranging from 20 mg to less than 500 mg of crystal modification A of the compound 1-(2,6-difluorobenzyl)-1H-1,2,3-triazole-4-carboxamide and a solid pharmaceutically-acceptable carrier, wherein crystal modification A is characterized by characteristic lines with interplanar spacings (d values) of 10.5 Å, 5.14 Å, 4.84 Å, 4.55 Å, 4.34 Å, 4.07 Å, 3.51 Å, 3.48 Å, 3.25 Å, 3.19 Å, 3.15 Å, 3.07 Å, and 2.81 Å, determined by means of an X-ray powder pattern.

2. The dosage form of claim 1, wherein dosage is in the form of a tablet.

3. The dosage form of claim 1, wherein the amount ranges from 200 to 400 mg.

4. The dosage form of claim 1, further comprising one or more excipients.

5. The dosage form of claim 1, wherein the amount of crystal modification A ranges from approximately 100 mg to 400 mg.

6. The dosage form of claim 1, wherein dosage is in the form of a solid for oral administration.

7. The solid dosage form of claim 1, further comprising a film-coat.

8. The solid dosage form of claim 1, wherein the amount of crystal modification A comprises a dosage unit comprising 200 mg.

9. The solid dosage form of claim 1, wherein the amount of crystal modification A comprises a dosage unit comprising 400 mg.

10. A tablet for oral administration comprising a therapeutically-effective amount of crystal modification A of the compound 1-(2,6-difluorobenzyl)-1H-1,2,3-triazole-4-carboxamide and microcrystalline cellulose wherein crystal modification A is characterized by characteristic lines with interplanar spacings (d values) of 10.5 Å, 5.14 Å, 4.84 Å, 4.55 Å, 4.34 Å, 4.07 Å, 3.51 Å, 3.48 Å, 3.25 Å, 3.19 Å, 3.15 Å, 3.07 Å, and 2.81 Å, determined by means of an X-ray powder pattern.

11. The tablet of claim 10, having a dosage unit of crystal modification A ranging from 200 mg to 400 mg.

12. A tablet for oral administration comprising a therapeutically-effective amount of crystal modification A of the compound 1-(2,6-difluorobenzyl)-1H-1,2,3-triazole-4-carboxamide, a pharmaceutically-acceptable carrier, and a film coat, wherein crystal modification A is characterized by characteristic lines with interplanar spacings (d values) of 10.5 Å, 5.14 Å, 4.84 Å, 4.55 Å, 4.34 Å, 4.07 Å, 3.51 Å, 3.48 Å, 3.25 Å, 3.19 Å, 3.15 Å, 3.07 Å and 2.81 Å, determined by means of an X-ray powder pattern.

13. The tablet of claim 12, having a dosage unit of crystal modification A ranging from 20 mg to less than 500 mg.

14. The tablet of claim 12, having a dosage unit of crystal modification A ranging from 200 mg to 400 mg.

15. The tablet of claim 12, having a dosage unit of crystal modification A comprising 200 mg.

16. The tablet of claim 12, having a dosage unit of crystal modification A comprising 400 mg.

17. The tablet of claim 12, wherein the pharmaceutically-acceptable carrier comprises microcrystalline cellulose.

18. The tablet of claim 12, wherein the pharmaceutically-acceptable carrier comprises sodium carboxymethylcellulose.

19. The tablet of claim 12, wherein the film coat comprises hydroxypropylmethylcellulose.

20. The tablet of claim 12, wherein the pharmaceutically-acceptable carrier comprises microcrystalline cellulose and the film-coat comprises hydroxypropylmethylcellulose.

21. The tablet of claim 12, wherein the pharmaceutically-acceptable carrier comprises sodium carboxymethylcellulose and the film-coat comprises hydroxypropylmethylcellulose.

* * * * *